United States Patent [19]

Lange, Jr.

[11] Patent Number: 4,496,761
[45] Date of Patent: Jan. 29, 1985

[54] PROCESS FOR MAKING CARBOHYDRAZIDE

[75] Inventor: Paul H. Lange, Jr., New Haven, Conn.

[73] Assignee: Olin Corporation, Cheshire, Conn.

[21] Appl. No.: 408,970

[22] Filed: Aug. 17, 1982

[51] Int. Cl.$^3$ ............................................ C07C 133/02
[52] U.S. Cl. .......................................... 564/37; 564/18
[58] Field of Search .................................... 564/18, 37

[56] References Cited

U.S. PATENT DOCUMENTS 4,269,717 5/1981 Slovinsky .

OTHER PUBLICATIONS

Byrkit et al., "Hydrazine in Organic Chemistry", Ind. Eng. Chem., vol. 4, pp. 1862–1875, (1950).

Audrieth et al., "Preparation and Properties of Thiocarbohydrazide", J. Org. Chem. 19, 733–748, (1954).
Curtius et al., Chem. Ber., 27, 55, (1894).
F. Kurzer and M. Wilkinson, "The Chemistry of Carbohydrazide and Thiocarbohydrazide", *Chemical Reviews*, vol. 70, American Chemical Society, pp. 111–149, (1970).
E. Mohr, J. Brezinski and L. Audrieth, "Carbohydrazide", *Inorganic Synthesis*, vol. IV, pp. 32–35, (1953).

*Primary Examiner*—Thomas A. Waltz
*Attorney, Agent, or Firm*—William A. Simons; Thomas P. O'Day

[57] ABSTRACT

Disclosed is a process for making carbohydrazide by reacting a di(lower alkyl) carbonate with hydrazine in two-stages with an intermediate step of removing the corresponding lower alkanol formed as a co-product in the first stage. The two reaction stages are carried out at relatively low temperatures (i.e. below about 80° C.).

10 Claims, No Drawings

PROCESS FOR MAKING CARBOHYDRAZIDE

BACKGROUND OF THE INVENTION

1. Field of the Invention

The present invention relates to a process for making carbohydrazide.

2. Description of the Prior Art

Carbohydrazide [NH$_2$NHC(O)NHNH$_2$] has recently been found to be an effective oxygen scavenger for boiler system. See U.S. Pat. No. 4,269,717, which issued to M. Slovinsky on May 26, 1981. It has also been used as a cross-linker for elastic-type fibers.

This compound has been prepared by numerous methods. See F. Kurzer and M. Wilkinson "The Chemistry of Carbohydrazide and Thiocarbohydrazide" *Chemical Reviews Volume* 70, American Chemical Society pages 111–149 (1970). The usual method for making carbohydrazide in commercial quantities was to react a dialkyl carbonate and excess hydrazine in one step. The alcohol co-product was simultaneously distilled off at atmospheric pressure until the reaction was complete. Typically, the reaction lasted from about 4 to about 6 hours and the temperature of the reaction mixture was raised from about 95° C. to about 120° C. See E. Mohr, J. Brezinski and L. Audrieth "Carbohydrazide" *Inorganic Synthesis, Volume IV,* McGraw-Hill Book Company, Inc. (1953) pages 32–35.

This prior art process sometimes resulted in carbohydrazide products which contained large amounts of impurities. The identities and effects of these impurites are not well understood. However, they contaminate the product and lower the yield, as well as cause some batches of carbohydrazide to unexpectedly decompose within a few months. This decomposition may have contributed to preventing the large scale commercial usage of carbohydrazide in the past.

It is believed that the relatively high temperatures of this prior art process may contribute to the formation of these impurities by side reactions.

Furthermore, the useful technique of vacuum distillation could not safely be employed with this prior art process because of the excess amounts of hydrazine present. Hydrazine vapor in the distillation column might form explosive mixtures if the apparatus leaked and air were admitted.

Accordingly, there is a need for a process for making carbohydrazide which forms smaller amounts of undesirable impurities and is safe to use with vacuum distillation or similar techniques. The present invention is a response to that need.

BRIEF SUMMARY OF THE INVENTION

The present invention, therefore, is directed to a process for making carbohydrazide which comprises:

(a) reacting hydrazine with a di(lower alkyl) carbonate at a temperature below about 80° C. for a sufficient amount of time to form a first reaction mixture comprising the corresponding lower alkyl carbazate and the corresponding lower alkanol;

(b) removing at least a portion of the lower alkanol from this first reaction mixture;

(c) then adding additional hydrazine to the remaining first reaction mixture and reacting a portion of this additional hydrazine with the lower alkyl carbazate at a temperature below about 80° C. for a sufficient amount of time to form a second reaction mixture comprising carbohydrazide, the corresponding lower alkanol, and unreacted hydrazine; and (d) recovering the carbohydrazide from the second reaction mixture.

DETAILED DESCRIPTION

The formation of carbohydrazide by the two-stage reaction of the present invention may be illustrated by the following equations (A) and (B) wherein dimethyl carbonate is employed as the di(lower alkyl) carbonate and hydrazine hydrate is the source of hydrazine:

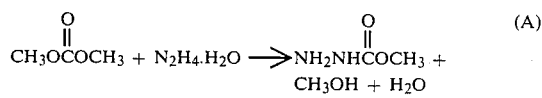

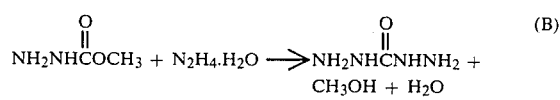

Any di(lower alkyl) carbonate having lower alkyl groups having one to about 4 carbon atoms may be employed. This would include methyl, ethyl, n-propyl, iso-propyl and n-butyl. Preferred di(lower alkyl) carbonates are dimethyl carbonate and diethyl carbonate. The most preferred di(lower alkyl) carbonate is dimethyl carbonate.

Any suitable source of hydrazine may be employed in the first reaction stage. Commercial solutions of hydrazine hydrate (i.e. aqueous solutions containing from about 30% to about 65% by weight hydrazine) may be used. Preferably, unreacted hydrazine from the second reaction stage may be recycled back to the first stage for reaction. To maintain a water balance, the water added in hydrazine hydrate solutions will be removed in step (b) along with the formed lower alkanol.

Hydrazine is added in the first stage to give a mole ratio of hydrazine to di(lower alkyl) carbonate in a range preferably from about 0.9:1 to about 1.1:1. Such mole ratios prevent substantial amounts of unreacted reactants from being removed with the lower alkanol co-product in the intermediate removal step (b). More preferably, this mole ratio is from about 0.95:1 to about 1.1:1 so that no hydrazine is left unreacted. Hydrazine has a potentially more harmful vapor than di(lower alkyl) carbonates.

As stated above, the temperature of this first reaction stage should be kept under about 80° C. This prevents the formation of unwanted by-products made by side reactions that occur at higher temperatures. Preferably, this stage of the reaction may be carried out at temperatures from 50° C. to about 75° C. The reaction time for this first stage, which is dependent mainly upon the specific temperature and mole ratio employed for this stage, should be sufficient to allow the reaction to be completed. With about a 1:1 mole ratio and a 70° reaction temperature, about 2 to 5 hours would be required.

After this first reaction stage is over, at least a portion (e.g. 25% by weight) of the lower alkanol co-product is removed. Preferably, at least a major portion (i.e. at least 50% by weight) is removed from the reaction mixture. More preferably, substantially all (i.e. at least 90% by weight) of both the lower alkanol (and any water) is removed. It is preferred that this removal be accomplished by vacuum distillation. This technique may be safe if no substantial amounts of hydrazine remain unreacted. Along with lower alkanol, water is also removed from the reaction system if hydrazine hydrate solutions are used as the source of hydrazine. When vacuum distillation is employed, it is preferred to carry out this distillation at a pressure from about 1 to about 100 mm Hg. Preferred distillation temperatures may vary from about 25° C. to about 70° C.

Upon the desired completion of the lower alkanol removal step, the second stage of reaction [see Equation (B), above] may proceed. In this second stage, additional hydrazine is added to the reaction mixture to complete the reaction. The temperature for the second stage, like the first stage, should be kept under about 80° C. to prevent the formation of unwanted by-products. Preferably, this second stage may also be carried out at temperatures from about 25° C. to about 75° C. The reaction time for this stage, which is dependent upon the specific temperature and mole ratio employed should be sufficient to allow substantially all (above 90% by weight) of the lower alkyl carbazate to be converted to carbohydrazide. If the mole ratio of hydrazine to carbazate is 2:1 and the temperature is 70° C., about 2 to 5 hours of reaction time is required.

Excess hydrazine is preferably added in this second stage because the reaction is slow otherwise. It is preferred to employ mole ratios of hydrazine added to lower alkyl carbazate in the range from about 1.5:1 to about 4:1. It is more preferable to have this mole ratio in the range from about 1.8:1 to 2.2:1 since that will result in a suitable excess of hydrazine to be recycled to the first reaction stage. The preferred source of this additional hydrazine for this stage may be all fresh hydrazine (e.g. hydrazine hydrate solutions). Alternatively, mixtures of fresh hydrazine and recycled unreacted hydrazine from past reaction batches may be used. The additional presence of water from the hydrazine hydrate does not have any substantial undesirable effect on these reactions (A) and (B), but it increases the energy needed to run the reactions.

During this reaction (B), carbohydrazide is formed in the reaction mixture. At the reaction temperatures above about 50° C. this compound is substantially soluble and is difficult to recover in high yields. Accordingly, after the reaction is complete, it is preferred to recover the carbohydrazide from the reaction mixture by first cooling the reaction mixture (e.g. cool from about 50° C. to about 75° C. down to about 0° C. to about 30° C.) to form crystals of carbohydrazide. This is followed by separating these carbohydrazide crystals from the reaction mixture. A preferred separation technique is filtration.

After the separation of these crystals, it is preferred to recycle the filtrate back to the first stage reaction [see Equation (A)] or to the second-stage reaction [see Equation (B)], or both, as a source of hydrazine. It is more preferred to recycle this filtrate back to only the first stage. The lower alkanol co-product of the second-stage reaction may be thus advantageously removed in the intermediate removal step. The additional water (from hydrazine hydrate) may also be removed from the system when the filtrate is recycled back to the first step.

If desired, the separated crystals of carbohydrazide may be further processed to obtain a dry, stable product. This may be achieved by washing the crystals with a lower alkanol (e.g. methanol, ethanol) and then drying the washed crystals. The amount of alkanol employed in the washing should be sufficient to remove all free hydrazine or until no more hydrazine is removed. The preferred drying technique is vacuum drying, which may be carried out at temperatures from about 40° C. to about 80° C. and at pressure from about 0.1 to 25 mm Hg., or greater.

The following Examples further illustrate the present invention. All parts and percentages are by weight unless explicitly stated otherwise.

EXAMPLE 1

A 2 liter 3-necked round bottom glass reaction vessel was charged with hydrazine hydrate (103 grams; 2.06 moles; 64% by weight hydrazine in aqueous solution) and dimethyl carbonate (195 grams; 2.145 moles; 99% pure liquid). The reaction was held at 50° C. for 20 minutes and then at 25° C. for 20 hours. After this time, no more hydrazine was detected in the reaction by vapor phase chromatography. Vacuum was applied by water aspiration and methyl alcohol, water and unreacted dimethyl carbonate were distilled off at about 25 to 30 mm Hg. At the end of distillation, the pot contained substantially methyl carbazate (185 grams; 2.06 moles).

In the second step of the reaction, hydrazine hydrate (255 grams; 5.1 moles; 64% by weight hydrazine in aqueous solution) was added. After heating at 70° C. for 4 hours, no more methyl carbazate was detected by vapor phase chromatography. Carbohydrazide was crystallized by cooling to 0° C. The carbohydrazide crystals were collected on a filter, rinsed with methyl alcohol and vacuum dried 1 hour at about 80° C. and 0.2 mm Hg.

The above reactions were kept under a nitrogen blanket in all steps until filtration. Filtration was done under air atmosphere.

The yield of carbohydrazide was 145 grams (1.61 moles). The conversion of dimethyl carbonate to product was 75%. The conversion of hydrazine hydrate to product was 45%. (Note: The unconverted hydrazine is used in the next cycle, giving a much higher overall conversion rate.) The carbohydrazide product assayed 99.8%±2% when made. After 5 months, the assay was 96.8%±2%. After 10 months, the assay was 94.1%±2% after 15 months, the assay was 96.7%±2%. The filtrate of mother liquor and rinse were combined for use in the next cycle (Example 2).

EXAMPLE 2

The combined filtrate and rinse from Example 1 (489 grams) containing hydrazine (approximately 96 grams; about 3 moles of $N_2H_4$), water, methanol and dissolved carbohydrazide was charged into a 2 liter 3-necked round bottom glass reaction vessel. Dimethyl carbonate (349 grams; 3.84 moles; 99% pure liquid) was added to the vessel and the mixture was heated from 37° to 68° C. over one hour. Then vacuum was applied and water, methyl alcohol and dimethyl carbonate were distilled off over 6.5 hours with pot temperature rising from 60° to 73° C. At the end of distillation, the vessel contained substantially methyl carbazate (180 g 3 moles).

In the second stage of the reaction hydrazine hydrate (362 grams; 7.24 moles; 64% hydrazine in aqueous solution) was added. The reaction was held at 70° C. for 4 hours, then carbohydrazide was crystallized by cooling to 5° C. The carbohydrazide crystals were collected on a filter, rinsed with methyl alcohol and dried under vacuum of 0.2 mm Hg at 80° C. for one hour.

The above reactions were kept under nitrogen blanket in all steps until filtration. Filtration was done under air atmosphere.

The yield of carbohydrazide was 256 grams (2.84 moles). 77% of the dimethyl carbonate was converted to carbohydrazide. 79% of the hydrazine was converted to carbohydrazide.

The carbohydrazide product assayed 100%±2% when made. After 5 months the assay was 96.6%±2%. After 10 months, the assay was 96.3%±2%. After 15 months, the assay was 96.5%±2%.

EXAMPLE 3

A 2 liter, 3-neck round bottom, glass reaction vessel was charged with hydrazine hydrate (222 grams; 4.44 moles; 64% hydrazine in aqueous solution) and diethyl carbonate (582 g; 4.88 moles; 99% pure liquid). The reaction was held at 56° to 67° C. for 2.2 hours. Vacuum was applied by vacuum pump and water, ethyl alcohol, and diethyl carbonate were distilled off. The maximum temperature in the pot was 65° C. At the end of the distillation the vessel contained substantially ethyl carbazate (462 grams; 4.44 moles).

In the second step of the reaction, hydrazine hydrate (375 grams, 7.5 moles, 64% hydrazine in aqueous solution) was added. The mixture was heated at 64° to 77° C. for 8 hours. Carbohydrazide was crystallized by cooling to 22° C. The carbohydrazide crystals were collected on a filter, rinsed with methyl alcohol and vacuum dried 16 hours at 45° C. and 0.5 mm Hg.

The above reactions were kept under a nitrogen blanket in all steps until filtration. Filtration was done under air atomsphere. The yield of carbohydrazide was 192 grams (2.13 moles). The conversion of diethyl carbonate to carbohydrazide was 43.4% complete. The conversion of hydrazide hydrate to carbohydrazide was 35.7% complete. Carbohydrazide assay was 95.0%±2%.

What is claimed is:

1. A process for making carbohydrazide comprising:
   (a) reacting hydrazine with a di(lower alkyl) carbonate at a temperature below about 80° C. for a sufficient amount of time to form a first reaction mixture comprising the corresponding lower alkyl carbazate and the corresponding lower alkanol, wherein the mole ratio of hydrazine added to di(lower alkyl) carbonate is from about 0.9:1 to about 1.1:1;
   (b) removing at least a portion of said lower alkanol from said first reaction mixture;
   (c) then adding additional hydrazine to said remaining first reaction mixture and reacting a portion of said additional hydrazine with said lower alkyl carbazate at a temperature below about 80° C. for a sufficient amount of time to form a second reaction mixture comprising carbohydrazide, the corresponding lower alkanol and unreacted hydrazine, wherein the mole ratio of hydrazine added to said lower alkyl carbazate is from about 1.5:1 to about 4:1; and
   (d) recovering said carbohydrazide from said second reaction mixture.

2. The process of claim 1 wherein said di(lower alkyl) carbonate is dimethyl carbonate.

3. The process of claim 1 wherein the reaction temperatures in step (a) is from about 50° C. to about 75° C.

4. The process of claim 1 wherein at least a major portion of said lower alkanol is removed from said first reaction mixture by vacuum distillation in step (b).

5. The process of claim 1 wherein at least a portion of the hydrazine added in step (c) is hydrazine hydrate.

6. The process of claim 1 wherein the reaction temperature of step (c) is from about 25° C. to about 75° C.

7. A process for making carbohydrazide comprising:
   (a) reacting hydrazine with a di(lower alkyl) carbonate in the presence of a temperature from about 50° C. to about 75° C. for a sufficient amount of time to form a first reaction mixture comprising the corresponding lower alkyl carbazate, the corresponding lower alkanol, and water, said mole ratio of hydrazine added to di(lower alkyl) carbonate added being from about 0.95:1 to about 1:1;
   (b) removing substantially all of both said lower alkanol and water from said first reaction mixture by vacuum distillation;
   (c) then adding additional hydrazine to said remaining first reaction mixture and reacting a portion of said additional hydrazine with said lower alkyl carbazate at a temperature from about 25° C. to about 75° C. for a sufficient amount of time to form a second reaction mixture comprising carbohydrazide, unreacted hydrazine, and the corresponding lower alkanol, and water; the mole ratio of additional hydrazine added to said lower alkyl carbazate being from about 1.8:1 to about 2.2:1;
   (d) cooling said second reaction mixture to a temperature from about 0° C. to about 30° C. to form crystals of carbohydrazide;
   (e) filtering said crystals of carbohydrazide from said second reaction mixture;
   (f) recycling at least a portion of said remaining second reaction mixture back to step (a), or step (c), or both, as a source of hydrazine,
   (g) washing said carbohydrazide crystals with a lower alkanol; and
   (h) drying said washed crystals to recover a dry, stable carbohydrazide product.

8. The process of claim 7 wherein said di(lower alkyl) carbonate is dimethyl carbonate.

9. The process of claim 8 wherein said vacuum distillation is carried out at a pressure from about 1 to about 100 mm Hg and at temperatures from about 25° to about 70° C.

10. The process of claim 9 wherein at least a portion of the hydrazine added in step (c) is hydrazine hydrate.

* * * * *